United States Patent [19] [11] 3,951,983
Danilewicz et al. [45] Apr. 20, 1976

[54] PHENOXYPROPANOLPIPERAZINES

[75] Inventors: John Christopher Danilewicz, Ash; John Edward Glyn Kemp, Canterbury; Michael Snarey, Sandwich; James Robert Wright, Deal, all of England

[73] Assignee: Pfizer Inc., New York, N.Y.

[22] Filed: Aug. 2, 1974

[21] Appl. No.: 494,206

Related U.S. Application Data

[62] Division of Ser. No. 196,729, Nov. 8, 1971, Pat. No. 3,856,794.

[30] Foreign Application Priority Data

Nov. 10, 1970 United Kingdom............... 53303/70

[52] U.S. Cl..................... 260/268 PH; 260/348 A; 260/348 R; 424/250
[51] Int. Cl.².................................... C07D 295/12
[58] Field of Search............................ 160/268 PH

[56] References Cited
UNITED STATES PATENTS 3,480,624  6/1975   Fouche........................ 260/268 TR
3,701,777  10/1972  Edenhofer et al............. 260/268 PH
3,856,794  12/1974  Danilewicz et al. .......... 260/268 PH

OTHER PUBLICATIONS

V. P. Arya et al., J. of Pharmaceutical Sciences, Vol. 58, No. 4, Apr. 1969, pp. 432–440.
P. C. Das et al., J. of Medicinal Chemistry, Vol. 14, No. 9, pp. 890–891, (1971).
Burger, Medicinal Chemistry, 2nd Ed. p. 42 (1960).

Primary Examiner—Joseph A. Narcavage
Assistant Examiner—Jose Tovar
Attorney, Agent, or Firm—Connolly and Hutz

[57] ABSTRACT

A series of novel substituted phenoxypropyl piperazine derivatives have been prepared by reacting the appropriate 1-phenoxy-2,3-epoxypropane compound with 1-phenoxy-3-(4-phenylpiperazine-1-yl)propan-2-ols suitable N-phenylpiperazine reagent. The resulting 1-phenoxy13-(4-phenylpiperazine-1-yl)propan-2-ols are useful in the field of chemotherapy as antihypertensive agents. Preferred members include compounds having an acetamidomethyl, carboxymethyl or carbamoylmethyl group substituted on the phenyl ring of the phenoxy moiety. Alternate methods of preparation are also provided.

9 Claims, No Drawings

PHENOXYPROPANOLPIPERAZINES

CROSS REFERENCE TO RELATED APPLICATION

This application is a division of application Ser. No. 196,729 filed Nov. 8, 1971 now U.S. Pat. No. 3,856,794 issued Dec. 24,1974.

BACKGROUND OF THE INVENTION

This invention relates to certain new and useful phenoxypropyl and phenylthiopropyl piperazine derivatives of principal interest to those in the field of chemotherapy. More particularly, it is concerned with various novel substituted 1-phenoxy-3-(4-phenylpiperazin-1-yl)propan-2-ols and their non-toxic acid addition salts, which are of especial value in view of their antihypertensive properties.

In the past, several attempts have been made by investigators in this particular field of therapy to obtain new and still better forms of agents and/or methods for the treatment of hypertension. In many instances, these efforts have further involved the synthesis and testing of various new and heretofore unavailable organic compounds, particularly in the area of the propanolamines. For instance, G. de Stevens et al. in U.S. Pat. No. 3,211,735 disclose a series of N-aryl-N'-oxyalkyl-diazacycloalkanes in this category that are reported to be active as antihypertensives, in addition to possessing adrenolytic and anti-inflammatory properties. Unfortunately, however, these particular prior art compounds also possess a number of disturbing drawbacks or side effects, which will effectively prohibit or at least seriously limit their use in medical therapy.

SUMMARY OF THE INVENTION

In accordance with the present invention, it has now been rather surprisingly found that certain novel 1-phenoxy- and 1-phenylthio-3-(4-phenylpiperazin-1-yl)propan-2-ol compounds are extremely useful when employed in the field of drug therapy as antihypertensive agents. The novel compounds of this invention are all selected from the group consisting of organic bases of the formula:

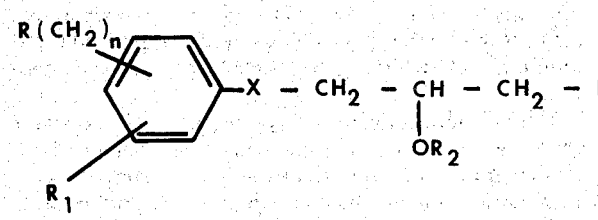

and the pharmaceutically acceptable acid addition salts thereof, wherein R is a member selected from the group consisting of hydroxy, amino, alkanoylamino having from one to six carbon atoms, acryloylamino, crotonoylamino, benzoylamino, phenylalkanoylamino having up to three carbon atoms in the alkanoyl moiety, succinoylimino, phthaloylimino, alkanesulfonamido having from one to six carbon atoms, benzenesulfonamido, p-toluenesulfonamido, carbamoyl, N-monoalkylcarbamoyl and N,N-dialkylcarbamoyl each having up to three carbon atoms in the alkyl moiety, N-phenylcarbamoyl, N-phenylalkylcarbamoyl having up to three carbon atoms in the alkyl moiety, sulfamoyl, N-monoalkylsulfamoyl and N,N-dialkylsulfamoyl each having up to three carbon atoms in the alkyl moiety, N-phenylsulfamoyl, N-phenylalkylsulfamoyl having up to three carbon atoms in the alkyl moiety, carboxy ad alkoxycarbonyl having from one to six carbon atoms in the alkoxy moiety; n is an integer of from one to two, inclusive; $R_1$ is a member selected from the group consisting of hydrogen, alkyl and alkoxy each having from one to six carbon atoms, fluorine, chlorine and bromine; $R_2$ is a member selected from the group consisting of hydrogen and alkanoyl having from two to six carbon atoms; $R_3$ is a member selected from the group consisting of phenyl and mono- and di-substituted phenyl wherein each substituent is chosen from the group consisting of alkyl and alkoxy having from one to six carbon atoms, fluorine, chlorine and bromine; and X is oxygen or sulfur. These novel phenoxypropanolpiperazine compounds all possess antihypertensive activity to a remarkably high degree and are therefore useful in the treatment of hypertensive conditions, in addition to being regulators of the cardiovascular system as well.

Of especial interest in this connection are the preferred compounds of the present invention where $R(CH_2)_n$ in the aforesaid structural formula is specifically located at either the 2- or 4-position of the phenyl ring and is preferably alkanoylaminomethyl having from one to six carbon atoms (and most preferably, acetamidomethyl) or it is carboxymethyl or carbamoylmethyl, and $R_1$ is hydrogen or it is alkyl having from one to six carbon atoms, $R_2$ is hydrogen, $R_3$ is chlorophenyl or it is alkoxyphenyl having from one to six carbon atoms in the alkoxy moiety (and most preferably, methoxy at the 2-position), and X is oxygen. Typical member compounds of the preferred class include such compounds as 1-(4-acetamidomethylphenoxy)-3-[4-(2-methoxyphenyl)piperazin-1-yl]-propan-2-ol, 1-(2-carboxymethylphenoxy-3-[4-(2-methoxyphenyl)-piperazin-1-yl]propan-2-ol, 1-(2-carbamoylmethylphenoxy)-3-[4-(2-methoxyphenyl)-piperazin-1-yl]propan-2-ol and 1-(2-methyl-4-carbamoylmethylphenoxy)-3-[4-(2-methoxyphenyl)piperazin-1 -yl]propan-2-ol, respectively. These particular compounds are all highly potent as regards their antihypertensive activity.

DETAILED DESCRIPTION OF THE INVENTION

In accordance with the process employed for preparing the novel compounds of this invention, an appropriately substituted 1-phenoxy-2,3-epoxypropane or the thiophenoxy analog thereof (where R is preferably other than amino) is reacted with a suitable N-phenylpiperazine reagent, which may or may not be further substituted on the phenyl ring as previously defined in $R_3$, to form the desired phenoxy-propanolpiperazine final product, in which case $R_2$ is always hydrogen. This particular reaction is normally carried out in the presence of a reaction-inert polar organic solvent such as a lower alkanol like methanol or ethanol, or an ether such as dioxane or tetrahydrofuran, etc., or mixtures of these. In general, the reaction is conducted at a temperature that is in the range of from about 20°C. up to about 100°C. for a period of about two to about 24 hours. It should be noted that the epoxy starting materials employed in this connection are, for the sake of time and convenience, most readily obtained from the corresponding phenols or thiophenols, as the case may be, by using standard organic reaction procedures well-known to those skilled in the art for the reaction of phenols with 2,3-epoxypropyl chloride.

Alternate methods of preparation for the compounds of this invention involve (1) reacting a N-phenylpiperazine reagent with a chlorohydrin or ether thereof (where $R_2$ is other than hydrogen) corresponding in structure to the 2,3-epoxide previously employed; and (2) reacting the appropriate phenoxy- or phenylthiopropanolamine reagent or an ether thereof with a suitable N,N-bis-(2-chloroethyl)aniline. In both instances, these particular routes are carried out by first dissolving the key reactants in a mutual solvent, such as ethanol, which must further contain a suitable amount of alkali reagent like sodium carbonate or bicarbonate, and thereafter heating the entire reaction mixture together, under reflux conditions, until the reaction in each instance is essentially complete.

As regards the substituted phenoxypropanolpiperazine compounds of the invention where R in the aforesaid structural formula is specifically amino, these are alternately and most preferably prepared by subjecting the corresponding amide final products (e.g., where R is acetamido, etc.) to acid hydrolysis. This step is readily achieved by refluxing the aforesaid amide product in aqueous hydrochloric acid and then recovering the amine compound by conventional means. In this way, 1-(4-acetamidomethylphenoxy)-3-[4-(2-methoxyphenyl)piperazin-1-yl]propan-2-ol is successfully converted to the corresponding 4-aminomethyl compound in a most facile manner. It should also be noted in this connection that compounds of the invention in which R is amino are additionally useful as intermediates for the preparation of other final products that can be subsequently derived therefrom. For instance, the 4-formamidoalkyl compounds are prepared by heating the corresponding aminoalkyl compounds with 90% formic acid in a suitable solvent. In like manner, the imido group is introduced at this point in the molecule by heating the 4-aminoalkyl compound with an anhydride of a suitable dicarboxylic acid, such as succinic acid or phthalic acid, while the use of an aliphatic or aromatic sulfonyl chloride as reagent in place of the anhydride leads, in turn, to the corresponding 4-sulfonamidoalkyl final products.

Alternatively, the foregoing aminoalkyl compounds may be prepared by chemical reduction of the corresponding carbamoyl compounds which are, in turn, earlier obtained by using either of the three general methods previously described. The reduction at hand is suitably effected in a dry organic solvent, like anhydrous diethyl ether or dry benzene, by merely employing such standard chemical reducing agents as lithium aluminum hydride or sodium di-(2-methoxyethoxy) aluminum hydride, etc. while preferably maintaining the system under reflux conditions. In this way, a compound such as 1-(2-carbamoylphenoxy)-3-[4-(2-methoxyphenyl)-piperazin-1-yl]propan-2-ol is converted to 1-(2-aminomethylphenoxy)-3-[4-(2-methoxyphenyl)piperazin-1-yl]propan-2-ol in a most facile manner.

Compounds of the invention in which R is a carboxy group may be prepared from those in which R is carbamoyl or alkoxycarbonyl, as previously defined, by merely subjecting the latter products to acid hydrolysis in accordance with standard organic procedure, e.g., by heating same in an aqueous hydrochloric acid solution (and preferably to the reflux temperature) until the reaction is essentially complete. The resulting carboxyalkyl compounds are, in turn, useful as intermediates leading to still other alkoxycarbonylalkyl compounds (via esterification), in addition to being highly active antihypertensive agents per se.

Compounds of the invention in which R is hydroxy may be prepared by chemical reduction of the corresponding carbalkoxy ester compounds where R is alkoxycarbonyl (e.g., methoxycarbonyl). This particular reduction step is readily accomplished in the same manner as was previously described for the conversion of the corresponding carbamoyl compounds to the aminoalkyl final products. The resulting hydroxyalkyl compounds in the present instance are all moderately potent antihypertensive agents.

Needless to say, compounds of the invention in which $R_2$ is alkyl of from one to six carbon atoms (i.e., ether derivatives) can also be prepared from compounds of the invention where $R_2$ is simply hydrogen by merely subjecting the latter unsubstituted phenoxypropanolpiperazines per se to conventional alkylation procedures well-known to those skilled in the art. In like manner, the esters of those compounds having free hydroxy groups (where $R_2$ is again hydrogen) can also be prepared by conventional procedure, starting from the aforesaid phenoxypropanolpiperazines per se and using standard esterification techniques to achieve the desired esters of this invention where $R_2$ is alkanoyl having from two to six carbon atoms.

Inasmuch as the phenoxypropanolpiperazine compounds of this invention all possess one asymmetric center, they may exist in separated d- and l-optically active forms, as well as in racemic or dl-mixtures necessarily produced by the various synthetic methods herein described. The present invention includes all these forms as being well within its scope. For instance, an optically active isomer may be obtained by simply resolving the racemic mixture at hand via the use of standard techniques well-known to those skilled in the art, e.g. by fractional crystallization of a phenoxypropanolpiperazine acid addition salt derived from an optically active acid. Alternatively, the optically active isomers may be prepared by using the appropriate enantiomers as starting materials in the foregoing reactions.

The pharmaceutically acceptable acid addition salts of the phenoxypropanolpiperazine base compounds of this invention are prepared by simply treating the corresponding organic bases with mineral and organic acids which form non-toxic acid addition salts having pharmacologically acceptable anions, such as the hydrochloride, hydrobromide, hydroiodide, sulfate or bisulfate, phosphate or acid phosphate, acetate, maleate, fumarate, oxalate, lactate, tartrate, citrate, gluconate, saccharate, methanesulfonate and p-toluenesulfonate salts.

As previously indicated, the phenoxypropanolpiperazine compounds of this invention are of especial value therapeutically when employed as antihypertensive agents, particularly in view of their ability to lower the blood pressure of hypertensive subjects to a statistically significant degree. For instance, 1-(2-carbamoylmethylphenoxy)-3-[4-(2-methoxyphenyl)piperazin-1-yl]-propan-2-ol, a typical and preferred agent of the present invention, has been found to consistently lower the blood pressure of conscious hypertensive dogs to a statistically significant degree when given by the oral route of administration, without showing any substantial signs of toxic side effects. The other compounds of this invention also cause similar results. Furthermore, all the herein described compounds of this invention can be administered by either the oral or parenteral routes of administration, for the present purposes at hand, without causing any significant untoward pharmacological side effects to occur in the subject to whom they are so administered. In general, these compounds are ordinarily administered at dosage levels ranging from about 0.15 mg. to about 5 mg. per kg. of body weight per day, although variations will necessarily occur depending upon the weight and condition of the subject being treated and the particular route of administration chosen.

In connection with the use of the phenoxypropanol-piperazine compounds of this invention for the treatment of hypertensive subjects, it is to be noted that these compounds may be administered alone, but generally will be administered in combination with a pharmaceutical carrier. The carrier is normally selected with regard to the intended route of administration as well as standard pharmaceutical practice. For example, these compounds may be administered orally in the form of tablets containing excipients such as starch or lactose, or in capsules either alone or on admixture with excipients, or else in the form of elixirs or suspensions containing flavoring agents or coloring matter, etc. For purposes of parenteral administration, they are best used in the form of a sterile aqueous solution of a previously enumerated water-soluble acid addition salt, which solution may also contain sufficient saline or glucose to render the final composition isotonic. These particular aqueous solutions are especially suitable for intravenous, intramuscular and subcutaneous injection purposes.

The activity of the compounds of the present invention, as antihypertensive agents, is determined by their ability to lower the blood pressure of experimental hypertensive animals when tested for hypotensive activity according to standard pharmacological practice and procedure [e.g, see Prioli et al. in the Journal of Applied Physiology, Vol. 15, p. 323 (1960)]. For example, these compounds are shown to reduce the blood pressure of conscious hypertensive rats when administered subcutaneously at a dose level of 10 mg./kg. and to reduce the blood pressure of conscious hypertensive dogs when administered orally at 20 mg./kg., respectively.

EXAMPLE I

A solution consisting of 4.4 g. of 1-[4-(2-carbamoylethyl)phenoxy]-2,3-epoxypropane and 3.8 g. of 1-(2-methoxyphenyl)piperazine dissolved in 30 ml. of ethanol was heated under reflux for a period of 6 hours. At the end of this time, the reaction mixture was cooled to room temperature and then diluted with sufficient diethyl ether to afford a buff-colored solid as precipitate. The latter material was subsequently extracted into 2N aqueous hydrochloric acid and isolated therefrom by basification of the resulting aqueous solution, followed by extraction with chloroform. The free base product thus obtained, viz., 1-[4-(2-carbamoylethyl)phenoxy]-3-[4-(2-methoxyphenyl)piperazin-1-yl]propan-2-ol, was then converted to the corresponding fumarate salt by treatment with fumaric acid in the usual manner. In this way, there were ultimately obtained white crystals of 1-[4-(2-carbamoylethyl)phenoxy]-3-[4-(2-methoxyphenyl)piperazin-1-yl]propan-2-ol hemifumarate, m.p. 177°–178°C. after recrystallization from isopropanol.

Anal. Calcd. for $C_{23}H_{31}N_3O_4 \cdot 0.5C_4H_4O_4$: C, 63.97; H, 7.05; N, 8.91. Found: C, 63.58; H, 7.09; N, 8.60.

EXAMPLE II

A solution consisting of 3.3 g. of 1-[4-(N-methylcarbamoylmethyl)phenoxy]-2,3-epoxypropane and 2.9 g. of 1-(2-methoxyphenyl)piperazine dissolved in 20 ml. of ethanol was maintained at ambient temperatures for a period of 3 days. At the end of this time, the resulting free base product, viz., 1-[4-(N-methylcarbamoylmethyl)phenoxy]-3-[4-(2-methoxyphenyl)piperazin-1-yl]propan-2-ol, was isolated as in Example I and thereafter converted to the fumarate salt to afford pure 1-[4-(N-methylcarbamoylmethyl)phenoxy]-3-[4-(2-methoxyphenyl)piperazin-1-yl]propan-2-ol hemifumarate, m.p. 106°–107°C. after recrystallization from isopropanol diisopropyl ether.

Anal. Calcd. for $C_{23}H_{31}N_3O_4 \cdot 0.5C_4H_4O_4$: C, 63.67; H, 7.05; N, 8.91. Found: C, 63.55; H, 7.44; N, 8.45.

EXAMPLE III

A solution consisting of 5.0 g. of 1-(2-carbamoylmethylphenoxy)-2,3-epoxypropane and 4.6 g. of 1-(2-methoxyphenyl)piperazine dissolved in 50 ml. of ethanol was allowed to stand at room temperature (~25°C.) for a period of approximately 16 hours. At the end of this time, the resultant precipitate was removed from the reaction mixture by means of suction filtration and subsequently recrystallized from ethyl acetate to give 1-(2-carbamoylmethylphenoxy)-3-[4-(2-methoxyphenyl)piperazin-1-yl]propan-2-ol as the pure free base compound, m.p. 120°–122°C.

Anal. Calcd. for $C_{22}H_{29}N_3O_4$: C, 66.14; H, 7.32; N, 10.52. Found: C, 66.17; H, 7.36; N, 10.46.

EXAMPLE IV

The procedure described in Example I was repeated except that 1-(4-carbamoylmethylphenoxy)-2,3-epoxypropane was employed as starting material in place of 1-[4-(2-carbamoylethyl)phenoxy]-2,3-epoxypropane, using the same molar basis as before, and a 3:1 by volume mixture of ethanol and dioxane replaced ethanol per se as the solvent of choice for the reaction. In this particular case, the corresponding final product thus obtained was 1-(4-carbamoylmethylphenoxy)-3-[4-(2-methoxyphenylpiperazin-1-yl]propan-2-ol, isolated as the pure free base compound, m.p. 147°–149°C.

Anal. Calcd. for $C_{22}H_{29}N_3O_4$: C, 66.14; H, 7.32; N, 10.37. Found: C, 66.50; H, 7.07; N, 10.52.

EXAMPLE V 1-(2-Carbamoylmethyl-4-methylphenoxy)-2,3-epoxypropane (3.0 g.) and 1-(2-methoxyphenyl)piperazine (2.6 g.) were both separately dissolved in ethanol and the two solutions were then mixed together to form a homogeneous system. The resultant clear mixture (50 ml.) was subsequently allowed to stand at ambient temperature for a period of 3 days, followed by evaporation under reduced pressure to give an oil which later solidified on cooling. After washing the latter material with diethyl ether and recrystallizing the crude base product from a mixture of ethyl acetate and petroleum ether, there were ultimately obtained crystals of pure 1-(2-carbamoylmethyl-4-methylphenoxy)-3-[4-(2-methoxyphenyl)piperazin-1-yl]propan-2-ol (isolated as the free base), m.p. 111°–113°C.

Anal. Calcd. for $C_{23}H_{31}N_3O_4$: C, 66.80; H, 7.56; N, 10.16. Found: C, 66.64; H, 7.77; N, 10.12.

EXAMPLE VI

The procedure described in Example V was repeated to prepare the following substituted 1-phenoxy-3-(4-phenylpiperazin-1-yl)propan-2-ol compounds, starting from the appropriate 1-phenoxy-2,3-epoxypropane and the corresponding N-phenylpiperazine reagent in each case:

1-(2-methyl-4-carbamoylmethylphenoxy)-3-[4-(2-methoxyphenyl)piperazin-1-yl]propan-2-ol, m.p. 134°–136°C.

1-(2-carbamoylmethylphenoxy)-3-[4-(2-ethoxyphenyl)piperazin-1-yl]propan-2-ol, m.p. 131°C.

1-(4-acetamidomethylphenoxy)-3-[4-(2-methoxyphenyl)piperazin-1-yl]propan-2-ol, m.p. 70°–73°C.

EXAMPLE VII

A solution consisting of 1.56 g. of 1-(2-carbamoylmethylphenoxy)-2,3-epoxypropane ($[\alpha]_D^{25}$ − 17°; C, 1% in ethanol) and 1.45 g. of 1-(2-methoxyphenyl)piperazine dissolved in 11.5 ml. of warm ethanol was maintained at ambient temperatures for a period of approximately 16 hours, followed by cooling to −5°C. After allowing the solution to stand at the latter point for a few hours, the resulting crystalline crops which successively formed were subsequently collected by means of suction filtration and thereafter combined and recrystallized rather extensively from ethanol to afford 2.21 g. of pure product, viz., 1-(2-carbamoylmethylphenoxy)-3-[4-(2-methoxyphenyl)piperazin-1-yl]propan-2-ol as the dextrorotatory free base compound (purity ascertained by thin layer chromatography). Conversion of the latter material to the corresponding hydrochloride salt on treatment with 0.1N hydrochloric acid (using the theoretical amount) then gave 1.87 g. of pure d-1-(2-carbamoylmethyl)-3-[4-(2-methoxyphenyl)piperazin-1-yl]propan-2-ol hydrochloride, m.p. 199°–200°C.; $[\alpha]_{DD}^{25} + 15°$ (C, 1% in water) after extensive recrystallization initially from isopropanol and then from ethanol Anal. Calcd. for $C_{22}H_{29}N_3O_4 \cdot HCl$: C, 60.61; H, 6.94; N, 9.64. Found: C, 60.58; H, 6.81; N, 9.76.

EXAMPLE VIII

A solution consisting of 9.0 g. of 1-(2-carbamoylphenoxy)-2,3-epoxypropane and 9.0 g. of 1-(2-methoxyphenyl)piperazine dissolved in 90 ml. of ethanol was allowed to stand at ambient temperatures for a period of approximately 16 hours. At the end of this time, the resultant crystalline precipitate was removed from the reaction mixture by means of suction filtration and subsequently recrystallized from aqueous methanol to give 12.5 g. of 1-(2-carbamoylphenoxy)-3-[4-(2-methoxyphenyl)piperazin-1-yl]propan-2-ol as the pure free base compound, m.p. 180°–182°C.

The product obtained as indicated above (12 g.) and 30 ml. of a 70% solution in benzene of sodium di(2-methoxyethoxy) aluminum hydride were added to 100 ml. of fresh dry benzene, and the resulting benzene solution was stirred at room temperature (~25°C.) for a period of one hour and then heated at the reflux point for an additional period of 1 hour. After allowing the spent reaction mixture to cool to room temperature, water was added to decompose excess hydride reagent and the benzene layer was then separated and subsequently evaporated in vacuo to afford a residual material. The latter product was then triturated with diethyl ether to give 8.5 g. of crystalline solid, which yielded pure 1-(2-aminomethylphenoxy)-3-[4-(2-methoxyphenyl)piperazin-1-yl]propan-2-ol (m.p. 113°–114°C.) after recrystallization from a mixture of ethyl acetate and petroleum ether. The yield of pure product was 3.2 g. from a total of 4 g. of unrecrystallized crystalline solid.

Anal. Calcd. for $C_{21}H_{29}N_3O_3$: C, 67.90; H, 7.87; N, 11.31. Found: C, 67.91; H, 7.83; N, 11.00.

EXAMPLE IX

A stirred mixture consisting of 3.7 g. of 1-(2-aminomethylphenoxy)-3-[4-(2-methoxyphenyl)piperazin-1-yl]propan-2-ol, 2.0 g. of potassium carbonate and 60 ml. of dry acetone was heated under reflux, while 1.2 g. of methanesulfonyl chloride were subsequently added thereto in a dropwise manner and with continued agitation. The resulting mixture was then refluxed for a period of 1 hour and ultimately evaporated to near dryness while under reduced pressure to give a residue. On trituration of the latter material with 100 ml. of water (in which it was stirred), there was subsequently obtained an oil from which the aqueous solution was thereafter readily decanted. The oil was then crystallized from a solution of aqueous ethanol to give 0.8 g. of 1-(2-methanesulfonamidomethylphenoxy)-3-[4-(2-methoxyphenyl)piperazin-1-yl]propan-2-ol, m.p. 170°–171°C.

Anal. Calcd. for $C_{22}H_{31}N_3O_5S$: C, 58.77; H, 6.95; N, 9.35. Found: C, 58.56; H, 7.07; N, 9.59.

EXAMPLE X

A solution consisting of 5.0 g. of 1-(2-carbamoylmethylphenoxy)-3-[4-(2-methoxyphenyl)piperazin-1-yl]propan-2-ol dissolved in 50 ml. of 40% aqueous hydrochloric acid was refluxed for a period of 2 hours and then allowed to cool to room temperature. Upon completion of this step, the resulting mixture was made basic with aqueous potassium carbonate solution and the solid material which precipitated at this point was thereafter collected by means of suction filtration and subsequently recrystallized from ethanol to afford the desired pure final product. After a further recrystallization from aqueous ethanol, there were ultimately obtained 1.5 g. of 1-(2-carboxymethylphenoxy)-3-[4-(2-methoxyphenyl)piperazin-1-yl]propan-2-ol, m.p. 170°–171°C.

Anal. Calcd. for $C_{22}H_{28}N_2O_5$: C, 65.98; H, 7.05; N, 7.00. Found: C, 65.54; H, 6.94; N, 6.61.

EXAMPLE XI

A solution consisting of 45 g. of 1-(2-carbamoylphenoxy)-3-[4-(2-methoxyphenyl)piperazinyl]propan-2-ol dissolved in 200 ml. of 40% aqueous hydrochloric acid was refluxed for a period of 2 hours and then allowed to cool to room temperature. Upon completion of this step, the resulting reaction mixture was adjusted to approximately pH 6–7 with aqueous potassium carbonate and the solid material which precipitated at this point was thereafter collected by means of suction filtration and subsequently recrystallized from aqueous ethanol to afford pure 1-(2-carboxyphenoxy)-3-[4-(2-methoxyphenyl)piperazin-1-yl]propan-2-ol, m.p. 198°–202°C. (analytical sample). The yield of crude product before recrystallization was 44 g. (98%).

Anal. Calcd. for $C_{21}H_{26}N_2O_5$: C, 65.27; H, 6.78; N, 7.25. Found: C, 64.98; H, 6.78; N, 7.17.

A solution of crude 1-(2-carboxyphenoxy)-3-[4-(2-methoxyphenyl)piperazin-1-yl]propan-2-ol (43 g.) in 250 ml. of methanol containing 25 ml. of concentrated sulfuric acid was refluxed for 1.5 hours and then allowed to cool to room temperature. Upon completion of this step, the resulting solution was concentrated in vacuo to a volume of approximately 100 ml., then poured into 250 ml. of water and made alkaline with aqueous sodium hydroxide solution. The latter basified solution was next thoroughly extracted with chloroform, and the chloroform extracts subsequently combined and dried over anhydrous magnesium sulfate. After removal of the drying agent by means of filtration and the solvent by means of evaporation under reduced pressure, there were ultimately obtained 34 g. of crude product as residual material. Crystallization of a portion of the latter material from methanol then gave pure 1-(2-methoxycarbonylphenoxy)-3-[4-(2-methoxyphenyl)piperazin-1-yl]propan-2-ol, m.p. 127°–128°C.

Anal. Calcd. for $C_{22}H_{28}N_2O_5$: C, 65.98; H, 7.05; N, 7.00. Found: C, 66.14; H, 7.15; N, 6.82.

To a well-stirred solution consisting of 10 ml. of sodium di(2-methoxyethoxy) aluminum hydride (a 70% solution in benzene) dissolved in 40 ml. of fresh dry benzene, there were added 6 g. of crude 1-(2-methoxycarbonylphenoxy)-3-[4-(2-methoxyphenyl)piperazin-1-yl]propan-2-ol and the resulting mixture was refluxed for a period of one-half hour. After allowing the spent reaction mixture to cool to room temperature, 2N aqueous sodium hydroxide solution was added to the mixture to decompose excess hydride reagent and the benzene layer was then separated and subsequently evaporated in vacuo to afford a solid product as residue. Crystallization of the latter material from a mixture of ethyl acetate and petroleum ether then gave 3.4 g. of pure 1-(2-hydroxymethylphenoxy)-3-[4-(2-methoxyphenyl)piperazin-1-yl]propan-2-ol, m.p. 120°–121°C.

Anal. Calcd. for $C_{21}H_{28}N_2O_4$: C, 67.72; H, 7.58; N, 7.52. Found: C, 67.61; H, 7.66; N, 7.89.

EXAMPLE XII

The following 1-phenoxy and 1-phenylthio-3-(4-phenylpiperazin-1-yl)propan-2-ol compounds are prepared by employing the procedures described in the previous examples, starting from readily available materials in each instance:

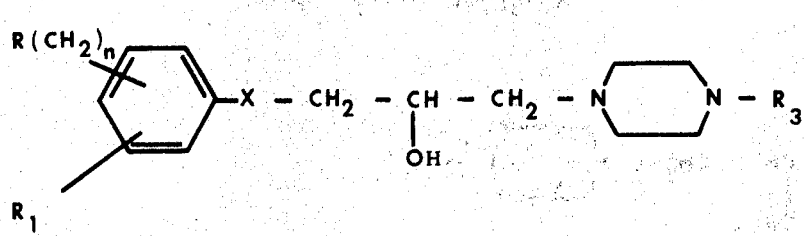

| R | n | $R_1$ | X | $R_3$ |
|---|---|---|---|---|
| 4-HO | one | 2-(n-$C_4H_9$) | S | 2,4-difluorophenyl |
| 4-$NH_2$ | two | 2-$OCH_3$ | O | 3-bromophenyl |
| 2-HCONH | two | H | O | 4-(n-hexyloxy)phenyl |
| 4-n-$C_5H_{11}$CONH | one | H | O | 3-(n-hexyloxy)phenyl |
| 3-$CH_2$=CHCONH | two | H | O | 2-chlorophenyl |
| 4-$CH_3$CH=CHCONH | one | H | O | 2-ethylphenyl |
| 5-$C_6H_5$CONH | two | 3-Br | S | 4-chlorophenyl |
| 4-$C_6H_5(CH_2)_3$-CONH | one | 2-$CH_3$ | O | 2,5-dimethoxyphenyl |
| 3-succinoylimino | two | H | O | 4-methylphenyl |
| 4-phthaloylimino | one | H | S | 2-methoxyphenyl |
| 4-n-$C_6H_{13}SO_2NH$ | one | 2-Cl | O | 3,4-dimethylphenyl |
| 2-$C_6H_5SO_2NH$ | two | H | O | 4-(n-butyl)phenyl |
| 4-p-$CH_3C_6H_4SO_2NH$ | one | H | S | 3,5-difluorophenyl |
| 2-$H_2NCO$ | one | H | O | 2-chlorophenyl |
| 4-$H_2NCO$ | two | 2-$CH_3$ | O | 4-(n-hexyloxy)phenyl |
| 3-iso-$C_3H_7$ NHCO | two | H | O | 2,4-dimethoxyphenyl |
| 4-$(CH_3)_2NCO$ | one | H | S | 4-chlorophenyl |
| 2-$C_6H_5NHCO$ | two | 4-Br | O | phenyl |
| 4-$C_6H_5(CH_2)_3$-NHCO | one | H | O | 2-ethoxyphenyl |
| 2-$H_2NSO_2$ | two | 4-$OC_6H_{13(n)}$ | O | 2-chlorophenyl |
| 3-n-$C_3H_7NHSO_2$ | one | H | S | 4-bromophenyl |
| 4-$(CH_3)_2NSO_2$ | two | 2-$OC_2H_5$ | O | 4-fluorophenyl |
| 3-$C_6H_5NHSO_2$ | one | H | O | 2,5-dimethoxyphenyl |
| 4-$C_6H_5(CH_2)_3NHSO_2$ | two | H | S | 4-(n-hexyl)phenyl |
| 2-HOOC | two | H | O | 2-methoxyphenyl |
| 4-n-$C_6H_{13}OCO$ | one | 2-F | O | phenyl |
| 4-HCONH | one | H | O | 2-methoxyphenyl |
| 2-n-$C_5H_{11}CONH$ | two | H | O | 2-methoxyphenyl |
| 2-$C_6H_5CH_2CONH$ | two | H | S | 3,5-dichlorophenyl |
| 3-$CH_3SO_2NH$ | two | 5-Br | O | 2,6-dimethylphenyl |
| 4-$H_2NCO$ | two | H | O | 3-chlorophenyl |
| 2-$H_2NCO$ | one | H | O | 2-(n-hexyloxy)phenyl |
| 2-(n-$C_3H_7)_2$ NCO | two | H | O | 2-$CH_3O$-5-methylphenyl |
| 2-$C_6H_5CH_2NHCO$ | two | H | S | 3-Cl-4-methylphenyl |
| 3-$CH_3NHSO_2$ | one | H | O | 2,4-dimethylphenyl |
| 4-(n-$C_3H_7)_2NSO_2$ | one | 2-$C_2H_5$ | O | 3-methoxyphenyl |
| 2-$C_6H_5CH_2NHSO_2$ | one | H | O | 2,5-difluorophenyl |
| 4-HOOC | one | H | O | 4-(n-hexyloxy)phenyl |
| 2-$CH_3OCO$ | two | 4-Cl | S | phenyl |
| 4-$H_2NCO$ | two | H | O | 2-methoxyphenyl |
| 2-$H_2NCO$ | one | 4-(n-$C_6H_{13}$) | O | 2-methoxyphenyl |

EXAMPLE XIII

Two grams of 1-(2-carbamoylmethylphenoxy)-3-[4-(2-methoxyphenyl)piperazin-1-yl]propan-2-ol are added to 20 ml. of anhydrous pyridine, followed by the immediate addition of 8.0 g. of acetic anhydride with stirring. The resulting solution is refluxed for a period of 5 minutes, cooled and subsequently poured into 50 ml. of ice water, basified with 2N aqueous sodium hydroxide solution and extracted with chloroform. The organic phase is then washed with water, dried over anhydrous sodium sulfate and evaporated to yield the crude product. After recrystallization from ethanol, there is obtained pure 1-(2-carbamoylmethylphenoxy)-3-[4-(2-methoxyphenyl)piperazin-1-yl]-2-acetoxypropane as final product.

In like manner, 1-(2-methyl-4-carbamoylmethylphenoxy)-3-[4-(2-methoxyphenyl)piperazin-1-yl]propan-2-ol is converted to 1-(2-methyl-4-carbamoylmethylphenoxy)-3-[4-(2-methoxyphenyl)piperazin-1-yl]-

2-propionoxypropane on treatment with propionic acid anhydride in the presence of pyridine, and 1-(4-acetamidomethylphenoxy)-3-[4-(2-methoxyphenyl)-piperazin-1-yl]propan-2-ol is converted to 1-(4-acetamidomethylphenoxy)-3-[4-(2-methoxyphenyl)-piperazin-1-yl]-2-(n-capronoxy)propane on treatment with caproic acid anhydride in the presence of pyridine. Other esters of this invention (i.e., compounds where $R_2$ in the structural formula is alkanoyl as previously defined) are similarly prepared.

EXAMPLE XIV

The non-toxic hydrohalide acid addition salts of each of the 1-phenoxy- and 1-phenylthio-3-(4-phenylpiperazin-1-yl)propan-2-ol base compounds of this invention reported previously, such as the corresponding hydrochloride, hydrobromide, and hydriodide salts, are each individually prepared by first dissolving the respective organic base compound in absolute ether and then adding a saturated solution of the appropriate hydrohalide gas in ethyl acetate to the aforementioned ethereal solution, whereupon the desired acid addition salt soon precipitates from said solution. In this way, 5.0 g. of 1-(2-carbamoylmethylphenoxy)-3-[4-(2-methoxyphenyl)piperazin-1-yl]propan-2-ol, obtained as a free base product in Example III, is converted via dry hydrogen chloride gas to the corresponding hydrochloride acid addition salt in almost quantitative yield.

EXAMPLE XV

The nitrate, sulfate or bisulfate, phosphate or acid phosphate, acetate, maleate, fumarate, oxalate, lactate, tartrate, citrate, gluconate, saccharate, methanesulfonate benzenesulfonate p-toluenesulfonate p-toluenefulfonate salts of each of the aforementioned 1-phenoxy-ad 1-phenylthio-3-(4-phenylpiperazin-1-yl)propan-2-ol base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition therefrom. In this manner, equimolar amounts of 1-(2-carbamoylmethylphenoxy)-3-[4-(2-methoxy-phenyl)piperazin-1-yl]propan-2-ol and concentrated sulfuric acid react to afford the corresponding sulfuric acid addition salt. In like manner, each of the other salts is also similarly prepared.

What is claimed is:

1. A compound of the formula:

or the pharmaceutically acceptable acid addition salts thereof, wherein R is a member selected from the group consisting of hydroxy, amino, alkanoylamino having from one to six carbon atoms, acryloylamino, crotonoylamino, benzoylamino, phenylalkanoylamino having up to three carbon atoms in the alkanoyl moiety, succinoylimino, phthaloylimino, alkanesulfonamido having from one to six carbon atoms, benzenesulfonamido, p-toluenesulfonamido, sulfamoyl, N-monoalkylsulfamoyl and N,N-dialkylsulfamoyl each having up to three carbon atoms in the alkyl moiety, N-phenylsulfamoyl, N-phenylalkylsulfamoyl having up to three carbon atoms in the alkyl moiety, carboxy and alkoxycarbonyl having from one to six carbon atoms in the alkoxy moiety; $n$ is an integer of from one to two, inclusive; $R_1$ is a member selected from the group consisting of hydrogen, alkyl and alkoxy each having from one to six carbon atoms, fluorine, chlorine and bromine; $R_2$ is a member selected from the group consisting of hydrogen and alkanoyl having from two to six carbon atoms; $R_3$ is chlorophenyl or alkoxyphenyl having from one to six carbon atoms in the alkoxy moiety; and X is oxygen or sulfur.

2. A compound as claimed in claim 1 wherein R is alkanoylamino having from one to six carbon atoms, $R_1$ and $R_2$ are each hydrogen, $R_3$ is alkoxyphenyl having from one to six carbon atoms in the alkoxy moiety and X is oxygen.

3. A compound as claimed in claim 1 wherein R is carboxy, $R_1$ and $R_2$ are each hydrogen, $R_3$ is alkoxyphenyl having from one to six carbon atoms in the alkoxy moiety and X is oxygen.

4. A compound as claimed in claim 1 wherein $R(CH_2)_n$ is at the 2-position of the phenyl ring, $R_1$ and $R_2$ are each hydrogen, $R_3$ is 2-methoxyphenyl and X is oxygen.

5. A compound as claimed in claim 1 wherein $R(CH_2)_n$ is at the 4-position of the phenyl ring, $R_1$ and $R_2$ are each hydrogen, $R_3$ is 2-methoxyphenyl and X is oxygen.

6. A compound as claimed in claim 1 wherein $R(CH_2)_n$ is at the 2-position of the phenyl ring, $R_1$ is alkyl at the 4-position having from one to six carbon atoms, $R_3$ is 2-methoxyphenyl and X is oxygen.

7. A compound as claimed in claim 1 wherein $R(CH_2)_n$ is at the 4-position of the phenyl ring, $R_1$ is alkyl at the 2-position having from one to six carbon atoms, $R_3$ is 2-methoxyphenyl and X is oxygen.

8. 1-(4-Acetamidomethylphenoxy)-3-[4-(2-methoxyphenyl)piperazin-1-yl]-propan-2-ol.

9. 1-(2-Carboxymethylphenoxy)-3-[4-(2-methoxyphenyl)piperazin-1-yl[propan-2-ol.

* * * * *